(12) United States Patent
Augustine et al.

(10) Patent No.: US 7,659,310 B2
(45) Date of Patent: Feb. 9, 2010

(54) METHODS OF ENHANCING SOLUBILITY OF AGENTS

(75) Inventors: John G. Augustine, Lynn, MA (US); Kaliappanadar Nellaiappan, Lexington, MA (US); Benjamin S. Isaacs, Andover, MA (US); Indu J. Isaacs, Andover, MA (US)

(73) Assignee: Formatech, Inc., Andover, MA (US)

( * ) Notice: Subject to any disclaimer, the term of this patent is extended or adjusted under 35 U.S.C. 154(b) by 45 days.

(21) Appl. No.: 11/591,660

(22) Filed: Oct. 27, 2006

(65) Prior Publication Data

US 2008/0102109 A1 May 1, 2008

Related U.S. Application Data

(63) Continuation of application No. PCT/US2005/014611, filed on Apr. 27, 2005, which is a continuation-in-part of application No. 10/834,816, filed on Apr. 27, 2004, now Pat. No. 7,345,093.

(60) Provisional application No. 60/666,623, filed on Mar. 31, 2005.

(51) Int. Cl.
*A61K 31/20* (2006.01)

(52) U.S. Cl. .......... 514/546; 514/11; 514/26; 514/165; 514/449; 424/400; 424/486; 424/450

(58) Field of Classification Search .......... 514/11, 514/25, 165, 449, 546, 730; 424/400, 450, 424/486
See application file for complete search history.

(56) References Cited

U.S. PATENT DOCUMENTS

| | | | | |
|---|---|---|---|---|
| 5,415,869 A | 5/1995 | Straubinger et al. | .......... | 424/450 |
| 5,580,575 A | 12/1996 | Unger et al. | .......... | 424/450 |
| 5,684,169 A | 11/1997 | Hamada et al. | .......... | 549/510 |
| 6,096,331 A | 8/2000 | Desai et al. | .......... | 424/422 |
| 6,538,020 B2 | 3/2003 | Joshi-Hangal et al. | .......... | 514/449 |
| 6,599,527 B1 | 7/2003 | Leigh et al. | | |
| 2002/0103254 A1 | 8/2002 | Joshi-Hangal et al. | | |
| 2002/0120015 A1 | 8/2002 | Dennis et al. | | |
| 2004/0071775 A1* | 4/2004 | Jiang et al. | .......... | 424/486 |

FOREIGN PATENT DOCUMENTS

| | | |
|---|---|---|
| EP | 0249561 | 12/1987 |
| EP | 0670166 | 9/1995 |
| EP | 0923943 | 6/1999 |
| EP | 1151755 | 11/2001 |
| WO | WO 95/12385 | 5/1995 |
| WO | WO 97/20041 | 6/1997 |
| WO | WO 97/30695 | 8/1997 |
| WO | WO 99/04787 | 2/1999 |
| WO | WO 99/13914 | 3/1999 |
| WO | WO 99/45918 | 9/1999 |
| WO | WO 99/49848 | 10/1999 |
| WO | WO 00/00179 | 1/2000 |
| WO | WO 00/03753 | 1/2000 |
| WO | WO 00/40238 | 7/2000 |
| WO | WO 00/71163 | 11/2000 |
| WO | WO 01/01960 | 1/2001 |
| WO | WO 01/30448 | 5/2001 |
| WO | WO 01/87345 | 11/2001 |
| WO | WO 02/07712 | 1/2002 |
| WO | WO 02/43765 | 6/2002 |
| WO | WO/02080883 | 10/2002 |
| WO | WO 03/033592 | 4/2003 |
| WO | WO 03/045357 | 6/2003 |

OTHER PUBLICATIONS

Nasongkla et al., Pharm. Res., vol. 20, No. 10, pp. 1626-1633, 2003.*
Baedelmeijer et al., *Cancer Chemother, Pharmacol.*, 49: 119-125 (2002).
O'Reilly et al., *Int'l. J. of Pharmaceutics*, 109(2): 147-154 (1994).
Pinnamaneni et al., *Pharmazie*, 57(5): 291-300 (2002).

* cited by examiner

*Primary Examiner*—Deborah D. Carr
(74) *Attorney, Agent, or Firm*—Jones Day

(57) ABSTRACT

This invention concerns novel methods of enhancing the solubility of a compound. Compositions prepared using such methods are also disclosed. Compositions prepared using the methods have various advantages over conventionally known compositions.

16 Claims, No Drawings

METHODS OF ENHANCING SOLUBILITY OF AGENTS

This application is a continuation under 35 U.S.C. § 120 of PCT/US2005/014611, filed Apr. 27, 2005, which is a continuation-in-part under 35 U.S.C. § 120 of U.S. patent application Ser. No. 10/834,816, filed Apr. 27, 2004, now U.S. Pat. No. 7,345,093 and which claims priority under 35 U.S.C. § 119(e) to U.S. Provisional Application No. 60/666,623, filed Mar. 31, 2005, all of which are incorporated herein by reference in their entireties.

1. FIELD OF THE INVENTION

This invention relates to methods of enhancing solubility of a compound in a medium and compositions comprising the compound.

2. BACKGROUND OF THE INVENTION

Solubility is one of the key determinants of the bioavailability of a pharmaceutical agent. The dissolution of pharmaceutical agents in a pharmaceutically acceptable medium is the most preferred manner of formulation to deliver therapeutic agents, and many drug candidates do not reach the market due to their poor solubility.

Many attempts have been made to improve the solubility of insoluble compounds; These approaches include: reduction of particle size of a compound using techniques such as micronization and nanosuspensions; modification of the crystal habit of a compound; complexation with other agents such as cyclodextrins; dispersion of a compound in a highly soluble carrier; and solubilization of a compound using surfactants. Pinnamaneni et al., *Pharmazie*, 57(5): 291-300 (2002).

Among others, carrier agents are commonly used to dissolve the compounds that are otherwise insoluble. Most of the commonly used carrier agents, in particular, polyoxyethylene sorbitan monooleate (Polysorbate 80) and CREMOPHOR® EL, exhibit various clinical side effects, especially in children and newborns. For example, the currently approved formulation of paclitaxel, a commonly prescribed anti-cancer agent, contains 51% CREMOPHO® EL and 49% ethanol. CREMOPHOR® EL is believed to cause hypersensitive reactions to paclitaxel treatments. In addition, CREMOPHOR® EL has been reported to decrease the bioavailability of paclitaxel. Baedelmeijer et al., *Cancer Cliemother. Pharmacol.*, 49: 119-125 (2002). This decrease in bioavailability necessitates the administration of higher doses of the paclitaxel formulation, which, in turn, results in a higher risk of hypersensitive reactions to the paclitaxel formulation. Moreover, in drug formulations, such as paclitaxel, in which ethanol is present in the formulation and high doses are required, acute ethanol toxicity is a concern.

Although there have been previous attempts to eliminate both CREMOPHOR® EL and ethanol in formulations of drug molecules (see, e.g., U.S. Pat. No. 5,415,869 (liposomal formulation), U.S. Pat. No. 5,580,075 (gas-filled liposomal formulation), U.S. Pat. No. 5,684,169 (complexation with cyclodextrin), U.S. Pat. No. 6,538,020 (fatty acid esterified with PEG), WO 99/13914 (HSA formulation) and U.S. Pat. No. 6,096,331 (protein shell containing oil)), a need still exists for a method to effectively solubilize a compound without the use of harmful agents, or modifying the compound itself.

In addition, there also exists a need for improved solubility of compounds outside the pharmaceutical context.

3. SUMMARY OF THE INVENTION

This invention is based, in part, on the inventors' discovery that a compound's solubility in a medium can be enhanced by forming de novo fatty acid or fatty alcohol derived micelles in the presence of the compound. Moreover, it was also found that it is possible to solubilize compounds by directly contacting the compounds with fatty acid salts. Accordingly, the first embodiment of this invention is directed to a method of enhancing the solubility of a compound, said method comprising: (a) contacting the compound with a fatty acid (for example, by either adding the compound to the fatty acid or adding the fatty acid to the compound) under conditions in which said fatty acid does not substantially form micelles; and then (b) altering said conditions such that said fatty acid forms micelles in the presence of the compound. In one embodiment, the compound is a hydrophobic compound. In a preferred embodiment, the amount of fatty acid is at least equimolar and, more preferably, is approximately equimolar, to the amount of the added base. In one embodiment, the resulting micellar solution can be further diluted with a diluent to achieve a desired concentration of the solubilized compound (i.e., the compound remains in solution upon addition of the diluent). In a preferred embodiment, the diluent is an aqueous diluent.

In particular embodiments, the conditions under which the fatty acid does not substantially form micelles are acidic conditions, e.g., having a pH of 1 to 5, 1 to 3, 2 to 4 or 2 to 5, most preferably having a pH of approximately 2. In addition, to initiate micelle formation, the conditions are preferably alkaline conditions, achieved, for example, by addition of a base. The alkaline conditions can be pH 8 to 12, 8 to 10, or 10 to 12, and, more preferably, approximately pH 8. Preferably, the base is added in an amount that is at least approximately equimolar to the amount of the fatty acid, more preferably, in an amount that is approximately equimolar to the amount of fatty acid. Specific examples of a base that can be used in connection with the methods of this invention include, but are not limited to, potassium, sodium and ammonia bases, more particularly, KOH, NaOH, $NH_4OH$, ethylamine, diethylamine, triethylamine and triethanolamine.

Although any fatty acid can be used in the methods of this invention, preferred fatty acids are those comprising a hydrocarbon chain having more than three carbon atoms. In preferred embodiments, the hydrocarbon chain has 4, 5, 6, 7, 8, 9, 10, 11 or 12 carbon atoms. In other embodiments the hydrocarbon chain has 3 to 12, 3 to 10, 3 to 8, 4 to 12, 4 to 8, or 4 to 6 carbon atoms. In other embodiments, the hydrocarbon chain has 13 or greater carbon atoms, up to approximately 30 carbon atoms. The hydrocarbon chain may be saturated or unsaturated or may be branched or unbranched. Specific examples of a fatty acid include, but are not limited to, propionic acid, butyric acid, n-valeric acid, hexanoic acid, heptanoic acid, caprylic acid, nonanoic acid, decanoic acid, undecanoic acid, n-dodecanoic acid, oleic acid, linolenic acid and linoleic acid. In particular embodiments, a mixture of two or more fatty acids, for example, but not limited to, two, three, four or five fatty acids, is used for de novo formation of micelles.

In another embodiment, a compound can be solubilized in a medium by direct dispersion within one or more of non-polyethylated fatty acid salts. Accordingly, this invention also encompasses a method of enhancing the solubility of a compound comprising contacting the compound with a fatty acid salt. In one embodiment, the compound is a hydrophobic compound. In another embodiment, the resulting solution can be further diluted with a diluent to achieve a desired concentration of the solubilized compound. In a preferred embodiment, the diluent is an aqueous solution.

Although any fatty acid salt can be used in the methods of this invention, preferred fatty acid salts are those comprising a hydrocarbon chain having more than three carbon atoms. In preferred embodiments, the hydrocarbon chain has 4, 5, 6, 7, 8, 9, 10, 11, or 12 carbon atoms. In other embodiments the hydrocarbon chain has 13 or a greater number of carbon atoms, and up to approximately 30 carbon atoms. The hydrocarbon chain may be saturated or unsaturated or may be branched or unbranched. Specific examples of a fatty acid salt include, but are not limited to, sodium or potassium salts of propionic acid, butyric acid, n-valeric acid, hexanoic acid, heptanoic acid, caprylic acid, nonanoic acid, decanoic acid, undecanoic acid, n-dodecanoic acid, oleic acid, linolenic acid and linoleic acid. In particular embodiments, a mixture of two or more fatty acid salts, for example, but not limited to two, three, four or five fatty acid salts, is used.

In another embodiment, this invention encompasses a method of enhancing the solubility of a compound, said method comprising: (a) contacting the compound with a fatty alcohol (for example, by either adding the compound to the fatty alcohol or adding the fatty alcohol to the compound) under conditions in which said fatty alcohol does not substantially form micelles; and then (b) altering said conditions such that said fatty alcohol forms micelles in the presence of the compound. In one embodiment, the compound is a hydrophobic compound. In another embodiment, the resulting micellar solution can be further diluted with a diluent to achieve desired concentration of the solubilized compound. In a preferred embodiment, the diluent is an aqueous diluent.

In one embodiment, the altering of conditions to initiate the formation of micelles comprises making the compound-fatty alcohol mixture acidic (e.g., having a pH of 1 to 5, 2 to 4 or 2 to 5, most preferably having a pH of approximately 5), for example, by addition of an acid. Preferably, the amount of acid is at least approximately equimolar to, and more preferably, is approximately equimolar to, the amount of the fatty alcohol. An example of an acid that can be used in connection of this method is, but not limited to, sulfuric acid. Finally, base is added to the fatty alcohol-compound-acid mixture, resulting in a final pH of 6 to 12, 6.5 to 9, or 7 to 8. Specific examples of a base that can be used in connection with this method include, but are not limited to, KOH and NaOH.

In another embodiment, the altering of conditions to initiate the formation of micelles comprises addition of sulfonate. Preferably, the sulfonate is added at least in an approximately equimolar amount to the amount of the fatty alcohol.

Although any fatty alcohol can be used in the methods of this invention, preferred fatty alcohols are those comprising a hydrocarbon chain having more than three carbon atoms. In preferred embodiments, the hydrocarbon chain has 4, 5, 6, 7, 8, 9, 10, 11, or 12 carbon atoms. In other embodiments the hydrocarbon chain has 13 or greater number of carbon atoms, up to approximately 30 carbon atoms. The hydrocarbon chain may be saturated or unsaturated or may be branched or unbranched. Specific examples of a fatty alcohol include, but are not limited to, octanol. In particular embodiments, a mixture of two or more fatty alcohols, for example, but not limited to, two, three, four or five fatty alcohols, is used for de novo formation of micelles.

Initially, fatty acid, fatty acid salt or fatty alcohol used in methods of the invention can be added at an equimolar amount to the amount of the compound to be solubilized. Thereafter, fatty acid, fatty acid salt or fatty alcohol can be added empirically until the desired solubilization of the compound is achieved.

In certain embodiments, solubilizing a compound using methods of this invention results in 2-fold, 5-fold, 10-fold, 50-fold, 100-fold, 200-fold, 300-fold, 400-fold, 500-fold, 600-fold, 700-fold, 800-fold, 900-fold, 1000-fold or higher solubility than the solubility of the compound in water. In another embodiment, solubilizing a compound using methods of this invention results in 2-fold, 5-fold, 10-fold, 50-fold, 100-fold, 200-fold, 300-fold, 400-fold, 500-fold, 600-fold, 700-fold, 800-fold, 900-fold, 1000-fold or higher solubility than the solubility of the compound in an organic solvent. In other embodiments, the maximum solubility of a compound is achieved where the fatty acids, fatty acid salts, or fatty alcohols of this invention have a chain length of 5 or more, 10 or more, 15 or more, 18 or more, or 25 or more carbon atoms.

Depending on the type of compounds to be solubilized, fatty acid salts used in the methods of the invention may be dissolved in any aqueous or isotonic solutions (e.g., saline, water for injection (WFI), dextrose in water (for example, 5% dextrose in water or D5W), lactated ringers, etc.) before the compounds to be solubilized are added. In some embodiments, fatty acids or fatty alcohols used in the methods of the invention may be dissolved in co-solvents, particularly, organic solvents, such as ethanol, polyethylene glycol, DMSO, and any other pharmaceutically acceptable solvent before the compounds to be solubilized are added. The resulting solution (ie., the compound solubilized in fatty acid salts dissolved in aqueous or isotonic solvents, or in fatty acid/fatty alcohol dissolved in co-solvents) may be diluted to desired concentrations using any acceptable solutions such as aqueous or isotonic solutions containing a base or an acid. Specific examples of the diluents include, but are not limited to, water, isotonic glycerol, and aqueous solution of a base (e.g., NaOH).

In other embodiments, the co-solvents used for the solubilization of the compounds may be removed before dilution, storage, or use, using any methods known in the art. Examples include, but are not limited to, rotary evaporation, spray drying, lyophilization, and vacuum drying.

The methods of the invention preferably result in at least 70%, 80%, 90%, 95% or 99% of the compound being in solution. In other embodiments, the methods of the invention preferably result in 20%, 30%, 50%, 100%, 150%, 200% or more increase in solubility of a compound as compared to the solubility of the same compound in a reference solvent, without using the methods of the invention, as determined by any methods known in the art. In one embodiment, the reference solvent is water. In another embodiment, the reference solvent is a solvent other than water, such as, but not limited to, an organic solvent.

In preferred embodiments, the solubilized compound is diluted in an aqueous medium, such as, but not limited to, saline, Water for Injection (WFI), 5% Dextrose in Water (D5W), lactated ringers, dextrose or any other isotonic diluent available in the art. In other embodiments, the solubilized compound may be diluted in any non-aqueous medium readily available in the art. In addition, formulations of the invention are stable (ie., the compound does not significantly degrade, aggregate or come out of solution) for at least 1 hour, 4 hours, 8 hours, 12, hours, 24 hours, 2 days, 3 days, 5 days, 7 days, 10 days, 2 weeks, one month or one year, preferably at room temperature, but may be at temperatures between 0° C. and room temperature, e.g., at 4° C., or even at elevated temperatures, such as 30° C., 38° C. or 40° C. The solutions of the invention preferably can be readily lyophilized (e.g., with lyophilization times of 12, 24, 36 or 48 hours, preferably, of 24 to 36 hours), in particular, in the absence of bulking agents and/or detergents or surfactants. The lyophilized product is also, preferably, readily reconstituted in an aqueous medium and can be reconstituted in less than 30 seconds, less than 1 minute, less than 5 minutes, less than 10 minutes or less than 30 minutes with at least 80%, 90%, 95%, or 99% recovery of the lyophilized compound. In other preferred embodiments, formulations of the invention do not contain or are not prepared using any one or more of the following: any toxic solvents, such as CREMOPHOR® EL, N-methylpyrrolidone, dimethylformamide, and DMSO; co-solvents such as ethanol or polyethylene glycol; co-detergents or co-surfactants, such as polysorbate 80 or vitamin E; oils, such as castor oil or corn oil; proteins such as HSA, which, in and of itself, is non-toxic, but has the potential to introduce adventitious viruses that may be associated with it based on its human origins; or any other biologic which is potential source of contamination.

The solubility of any compounds can be enhanced using the methods of this invention. Specific examples include, but are not limited to, cyclosporin A, paclitaxel, ketoprofen, acetylsalicylic acid, propofol, β-Lapachone and digoxin. In addition, methods of this invention can be employed to obtain an increased solubility of non-hydrophobic compounds. Therefore, in some embodiments, the solubility of a non-hydrophobic compound can be enhanced using methods of this invention.

Formulations comprising a compound, or an acceptable salt, solvate, hydrate, clathrate or prodrug thereof, when prepared using the methods of this invention, were discovered to have various advantages over the compositions of the same compound known in the art. For example, the solubility of the compound is higher than the conventionally known compositions of the same compound when methods of this invention are used. Accordingly, in one embodiment, this invention is directed to a pharmaceutical composition comprising paclitaxel, or a pharmaceutically acceptable salt, solvate, hydrate, clathrate or prodrug thereof, wherein the concentration of paclitaxel, or the salt, solvate, hydrate, clathrate or prodrug thereof, solubilized is greater than 6 mg/mL. In another embodiment, this invention encompasses a pharmaceutical composition comprising cyclosporin A, or a pharmaceutically acceptable salt, solvate, hydrate, clathrate or prodrug thereof, wherein the concentration of cyclosporin A, or the salt, solvate, hydrate, clathrate or prodrug thereof, solubilized is greater than 50 mg/mL. In another embodiment, this invention encompasses a pharmaceutical composition comprising ketoprofen, or a pharmaceutically acceptable salt, solvate, hydrate, clathrate or prodrug thereof, wherein the concentration of ketoprofen, or the salt, solvate, hydrate, clathrate or prodrug thereof, solubilized is greater than 100 mg/mL. In yet another embodiment, this invention encompasses a pharmaceutical composition comprising acetylsalicylic acid, or a pharmaceutically acceptable salt, solvate, hydrate, clathrate or prodrug thereof, wherein the concentration of acetylsalicylic acid, or the salt, solvate, hydrate, clathrate or prodrug thereof, solubilized is greater than 25 mg/mL. In yet another embodiment, this invention encompasses a pharmaceutical composition comprising digoxin, or a pharmaceutically acceptable salt, solvate, hydrate, clathrate or prodrug thereof, wherein the concentration of digoxin, or the salt, solvate, hydrate, clathrate or prodrug thereof, solubilized is greater than 1 mg/mL.

Moreover, it was discovered that compositions prepared using the methods of this invention are more stable than the compositions prepared using conventional techniques known in the art, i.e., the active ingredient (the compound solubilized using methods of the invention) remains solubilized at, for example, room temperature, for a period longer than the compositions containing the same compound, but prepared using other known methods. Therefore, another embodiment of this invention is directed to a stable pharmaceutical composition comprising paclitaxel, cyclosporin A, ketoprofen, acetylsalicylic acid or digoxin. Specifically, greater than about 70 percent, about 80 percent and about 90 percent of the solubilized paclitaxel, cyclosporin A, ketoprofen, acetylsalicylic acid, propofol, β-Lapachone or digoxin remains solubilized after one week at room temperature.

Another advantage of the formulations prepared using the methods of this invention is that no harmful substances need to be used in the preparation. In one embodiment, this invention encompasses a pharmaceutical composition comprising paclitaxel, cyclosporin A, ketoprofen, acetylsalicylic acid, propofol, β-Lapachone or digoxin, which contains no additional co-solvent, detergent, surfactant, oil or proteins.

The pharmaceutical compositions of this invention can further comprise one or more excipients. The compositions can be prepared suitable for any route of administration, including, but not limited to, oral, mucosal (such as nasal or pulmonary), topical, trarsdermal and parenteral administration.

3.1 Definitions

As used herein, and unless otherwise specified, the term "enhance" or "enhancing," when used in connection with the solubility of a compound, means that the methods of this invention result in an increased solubility of the compound as compared to the solubility of the same compound in water. Specifically, the term "enhance" or "enhancing" means that, when the methods of this invention are used, the solubility of a compound increases about 20 percent or more, about 40 percent or more, about 60 percent or more, about 80 percent or more, about 100 percent or more, or 200 percent or more of the solubility of the same compound in a reference solvent. In some embodiments, the reference solvent is water. In other embodiments, the reference solvent is a solvent other than water, such as, but not limited to, an organic solvent.

As used herein, and unless otherwise specified, the term "hydrophobic compound" means a compound with little or no water solubility. In some embodiments, a hydrophobic compound has an intrinsic water solubility (i.e., water solubility of the unionized form) of less than about 20 percent by weight, about 15 percent by weight, about 10 percent by weight, about 5 percent by weight, about 1 percent by weight, about 0.1 percent by weight or about 0.01 percent by weight. In other embodiments, a hydrophobic compound has an intrinsic water solubility of less than about 10 mg/mL, about 7 mg/mL, about 5 mg/mL, about 3 mg/mL, about 1 mg/mL or about 0.1 mg/mL.

As used herein, or unless otherwise specified, the term "diluent" means any medium acceptable for the final use of a compound solubilized using methods of the invention. Accordingly, the term "diluent" includes, but is not limited to, any acceptable pharmaceutical, cosmetic, industrial, consumer-product-related, food-related, or dietary supplement-related media, or any other media available in the art. The term "diluent" encompasses both an aqueous and a non-aqueous medium.

As used herein, or unless otherwise specified, the term "aqueous medium" means any water based medium, e.g., water, saline solution, a sugar solution, a transfusion solution, a buffer, and any other readily available water-based medium. Further, an aqueous medium may contain one or more water soluble organic solvents. In the case of a parenteral solution, an aqueous medium is preferably sterile and suitable for use as a carrier of an active agent. Examples of an aqueous medium include, but are not limited to, water for injection, saline solution, Ringer's solution, D5W or other solutions of water-miscible substances such as dextrose and other electrolytes.

As used herein, and unless otherwise specified, the term "fatty acid" means a compound whose structure is a carboxylic group attached to a hydrocarbon chain having one or more carbon atoms. The hydrocarbon chain may be saturated or unsaturated. Also, the hydrocarbon chain may be straight or branched. Moreover, in some embodiments, hydrogens in the hydrocarbon chain may be substituted.

As used herein, and unless otherwise specified, the term "fatty alcohol" means a compound whose structure is an alcohol group attached to a hydrocarbon chain having one or more carbon atoms. The hydrocarbon chain may be saturated or unsaturated. Also, the hydrocarbon chain may be straight or branched. Moreover, in some embodiments, hydrogens in the hydrocarbon chain may be substituted.

As used herein, and unless otherwise specified, the term "fatty acid salt" means a compound formed from a reaction between a fatty acid and an inorganic/organic base. In addition, the term also encompasses a compound formed from a reaction between a fatty alcohol and an inorganic/organic acid. Examples of such acids include, but are not limited to, sulfuric and phosphoric acid. The hydrocarbon chain of the fatty acid salt may be saturated or unsaturated. In addition, the hydrocarbon chain may be straight or branched. Moreover, in some embodiments, hydrogens in the hydrocarbon chain may be substituted.

As used herein, and unless otherwise specified, the term "equimolar," when used in connection with the addition of an acid to a base, or vice versa, means that the hydrogen ions resulting from the acid and hydroxide ions resulting from the base are equimolar.

As used herein, and unless otherwise specified, the term "substituted" means a group substituted by one or more substituents such as, but not limited to, alkyl, alkenyl, alkynyl, cycloalkyl, aroyl, halo, haloalkyl (e.g., trifluoromethyl), substituted or unsubstituted heterocycloalkyl, haloalkoxy (e.g., trifluoromethoxy), hydroxy, alkoxy, cycloalkyloxy, heterocylooxy, oxo, alkanoyl, aryl, substituted aryl, substituted or unsubstituted heteroaryl (such as, indolyl, imidazolyl, furyl, thienyl, thiazolyl, pyrrolidyl, pyridyl, pyrimidyl and the like), arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloaamino, mono- and di-substituted amino, alkanoylamino, aroylamino, aralkanoylamino, substituted alkanoylamino, substituted arylamino, substituted aralkanoylamino, carbamyl (e.g., $CONH_2$), substituted carbamyl (e.g., CONH-alkyl, CONH-aryl, CONH-arylalkyl or instances where there are two substituents on the nitrogen), carbonyl, alkoxycarbonyl, carboxy, cyano, ester, ether, guanidino, nitro, sulfonyl, alkylsulfonyl, arylsulfonyl, arylalkylsulfonyl, sulfonamido (e.g. $SO_2NH_2$), substituted sulfonamido, thiol, alkylthio, arylthio, arylalkylthio, cycloalkylthio, heterocyclothio, alkylthiono, arylthiono and arylalkylthiono.

As used herein, and unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, and unless otherwise specified, the term "alkenyl" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, and unless otherwise specified, the term "alkynyl" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alknyl group can be unconjugated or conjugated to another unsaturated group. An alkynyl group can be unsubstituted or substituted.

As used herein, and unless otherwise specified, the term "pharmaceutically acceptable salt" refers to a salt prepared from pharmaceutically acceptable non-toxic acids or bases including inorganic acids and bases and organic acids and bases. Suitable pharmaceutically acceptable base addition salts for the compositions of the present invention include, but are not limited to metallic salts made from aluminum, calcium, lithium, magnesium, potassium, sodium and zinc or organic salts made from lysine, N,N'-dibenzylethylenediarine, chloroprocaine, choline, diethanolarnine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein, and unless otherwise indicated, the term "prodrug" means a derivative of a compound that can hydrolyze, oxidize, or otherwise react under biological conditions (in vitro or in vivo) to provide an active compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. Esterifying any of the carboxylic acid moieties present on the molecule conveniently forms the carboxylate esters. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, and unless otherwise specified, the term "stable," when used in connection with a formulation, means that the active ingredient (i.e., a compound solubilized using methods of the invention) of the formulation, when prepared using the methods of this invention, remains solubilized for a specified amount of time and does not significantly degrade or aggregate or become otherwise modified (e.g., as determined, for example by HPLC). In some embodiments, about 70 percent or greater, about 80 percent or greater or about 90 percent or greater of the compound remains solubilized after a week after dilution with an acceptable diluent at an elevated temperature (about 35° C. or higher). In other embodiments, about 70 percent or greater, about 80 percent or greater or about 90 percent or greater of the compound remains solubilized after a week after dilution with an acceptable diluent at room temperature. In other embodiments, about 70 percent or greater, about 80 percent or greater or about 90 percent or greater of the compound remains solubilized after a week at a reduced temperature (about 10° C. or lower).

As used herein, and unless otherwise specified, the term "harmful ingredient," when used in connection with pharmaceutical compositions, means an ingredient commonly used in a pharmaceutical composition that may cause clinical side effects such as, but not limited to, hypersensitive reaction, peripheral neuropathies, and/or decrease in the bioavailability of the active ingredient of the composition. Examples of harmful ingredients include, but are not limited to: toxic solvents such as CREMOPHOR® EL; co-solvents such as ethanol or PEG; co-detergents or surfactants such as polysorbates or vitamin E; oils such as Castor oil or corn oil; proteins such as HSA; or any other biologic which is potential source of contamination.

4. DETAILED DESCRIPTION OF INVENTION

4.1 Methods of Solubilization

This invention is based, in part, on the discovery that the solubility of a compound can be significantly enhanced when fatty acid or fatty alcohol derived micelles are formed de novo in the presence of the compound. Without being limited by a particular theory, it is believed that the enhanced solubility of the compound is the result of the initial association of the alkyl/alkene/alkyne group of the fatty acid or fatty alcohol and the compound. Upon the formation of a salt, which has associated with the compound, the fatty acid or the fatty alcohol can then effectively disperse the medium. Accordingly, a crucial step in the methods of this invention is the de novo synthesis of fatty acid or fatty alcohol salt derived-micelles in the presence of the compound. By way of an example, the solubility of Cyclosporin A in Oleic acid-NaOH is 50 mg/mL, which is 8,333 fold higher than the solubility of Cyclosporin in water. The resulting micellar solution can be further diluted with a diluent to achieve a desired concentration of the solubilized compound.

Alternatively, it was also discovered that compounds can be solubilized simply by contacting the compounds with one or more of non-polyethylated fatty acid salts. Without being limited by a particular theory, it is believed that the compounds can be effectively dispersed into micelles formed from fatty acid salts prior to the addition of the compounds. By way of an example, the solubility of paclitaxel in sodium caprylate is 2 mg/mL, which is 200 fold higher than the solubility of paclitaxel in water. When the carbon chain length of the fatty acid is increased to 18 (as in solutions containing sodium oleate or, sodium linoleate or sodium linolenate) the solubility is increased to 5.5 to 7.5 mg/mL paclitaxel, which is 550 to 750 fold higher than the solubility of paclitaxel in water. The resulting solution can be further diluted with a diluent to achieve a desired concentration of the compound.

Apart from an increased solubility, the methods of this invention provide many advantages over methods of solubilization conventionally known in the art. For example, the methods of this invention eliminate or reduce the need for toxic solvents such as CREMOPHOR® EL, N-methylpyrrolidone, dimethylformamide, and DMSO in the formulation. Furthermore, co-solvents such as ethanol or PEG, co-detergents or co-surfactants such as polysorbates or vitamin E, oils such as Castor oil or corn oil, and proteins such as HSA are not necessary for the solubilization of a compound according to the methods of this invention. Therefore, the methods of this invention provide an easy and convenient way to solubilize a compound, while providing a safer resulting formulation, by eliminating many harmful additives currently used for the solubilization of a compound. In addition, fatty acid salt mixtures provide other advantages in clinical settings, such as promoting an increase in drug permeability and inactivation of life-threatening virus particles that may be present in pharmaceutical compositions.

Moreover, the solubilized products obtained using the methods of this invention are either stable in solution or are readily lyophilized without requiring any bulking agents or detergents/surfactants. Moreover, lyophilization times are commercially viable, and the lyophilized product is readily reconstituted in an aqueous medium such as water, 0.9% saline or 5% dextrose.

In one embodiment, this invention encompasses a method of enhancing the solubility of a compound, said method comprising: (a) contacting the compound with a fatty acid under conditions in which said fatty acid does not substantially form micelles (either by adding the compound to the fatty acid or vice versa); and then (b) altering said conditions such that said fatty acid forms micelles in the presence of the compound. In one embodiment, the compound is a hydrophobic compound. In specific embodiments, the base and fatty acid are present in approximately equimolar amounts. In a specific embodiment, the methods of this invention further encompass diluting the resulting solution to achieve desired concentration of the compound.

Any methods known in the art can be used to initiate salt formation from the fatty acid, and, thus, initiate the formation of the micelles. In one specific embodiment, the compound-fatty acid mixture is in an acidic environment which does not promote micelle formation and then the environment is made alkaline such that the fatty acid forms micelles, for example by addition of a base. Although any base can be added to effectively initiate the formation of micelles, some specific examples of a base that can be used in connection with the methods of this invention include, but are not limited to, potassium, sodium and ammonia bases, more particularly, KOH, NaOH, $NH_4OH$, ethylamine, diethylamine, triethylamine and triethanolamine. In one embodiment, the base is added in at least an approximately equimolar amount to the amount of the fatty acid. In a specific embodiment, the base is added in an approximately equimolar amount to the amount of the fatty acid.

A wide variety of fatty acids can be effectively used in connection with the methods of this invention as long as the structure wherein a carboxylic group attached to a hydrocarbon chain is present. Although there is no limit as to the length of the hydrocarbon chain present in the fatty acid, in some embodiments, the hydrocarbon has three or more, ten or more, twenty or more, or twenty-five or more carbons. In some embodiments, the hydrocarbon chain may be saturated or unsaturated. In other embodiments, the hydrocarbon chain may be straight or branched. In other embodiments, one or more hydrogen atoms in the hydrocarbon chain may be substituted with other chemical moieties. Specific examples of a fatty acid that can be used in connection with the methods of this invention include, but are not limited to, propionic acid, butyric acid, n-valeric acid, hexanoic acid, heptanoic acid, caprylic acid, nonanoic acid, decanoic acid, undecanoic acid, n-dodecanoic acid, oleic acid, linoleic acid or linolenic acid.

In another embodiment, the solubility of a compound can be enhanced by simply contacting the compound with one or more of non-polyethylated fatty acid salts. Accordingly, this invention also encompasses a method of enhancing the solubility of a compound comprising contacting the compound with a fatty acid salt. In one embodiment, the compound is a hydrophobic compound. The resulting solution can be further diluted with a diluent to achieve a desired concentration of the compound.

Although any fatty acid salt can be used in the methods of this invention, preferred fatty acid salts are those comprising a hydrocarbon chain having more than three carbon atoms. In preferred embodiments, the hydrocarbon chain has 4, 5, 6, 7, 8, 9, 10, 11, or 12 carbon atoms. In other embodiments the hydrocarbon chain has 13 or a greater number of carbon atoms, up to approximately 30 carbons. The hydrocarbon chain may be saturated or unsaturated or may be branched or unbranched. Specific examples of a fatty acid salt include, but are not limited to: sodium or potassium salt of propionic acid, butyric acid, n-valeric acid, hexanoic acid, heptanoic acid, caprylic acid, nonanoic acid, decanoic acid, undecanoic acid, n-dodecanoic acid, oleic acid, linolenic acid or linoleic acid; or acid addition salts of fatty acids such as fatty acid sulfate and fatty acid phosphate. In particular embodiments, a mixture of two or more fatty acid salts, for example, but not limited to, two, three, four or five fatty acid salts, is used.

By way of an example, the direct solubilization of paclitaxel in an alkyl sulfate (e.g. sodium lauryl sulfate) results in the solubilization of 6.3 mg/mL to 8.5 mg/mL paclitaxel, which is 630-fold to 850-fold greater than the solubility of paclitaxel in water. In one embodiment, the resulting solution can be further diluted with a diluent to achieve desired concentration of the solubilized compound.

In another embodiment, this invention encompasses a method of enhancing the solubility of a compound, said method comprising: (a) contacting the compound with a fatty alcohol under conditions in which said fatty alcohol does not substantially form micelles (either by adding the compound to the fatty alcohol or vice versa); and then (b) altering said conditions such that said fatty alcohol forms micelles in the presence of the compound. In one embodiment, the compound is a hydrophobic compound. In specific embodiments, the acid and fatty alcohol are present in approximately equimolar amounts.

In a specific embodiment, the methods of this invention further encompass diluting the resulting solution with a diluent to achieve desired concentration of the compound.

Any methods known in the art can be used to initiate the formation of fatty alcohol salt, and thus formation of the micelles. In one specific embodiment, altering the conditions such that the fatty alcohol forms micelles encompasses addition of an acid, followed by addition of a base, i.e., making the fatty alcohol-compound mixture acidic and then adding a base to neutralize or even make the mixture alkaline. Although any combinations of an acid and a base can be added to effectively form a salt from the fatty alcohol and initiate the formation of micelles, an example of the acid used in connection with the methods of this invention includes sulfuric acid. Some specific examples of a base that can be used in connection with the methods of this invention include, but are not limited to, KOH, NaOH and $NH_4OH$. In one embodiment, the base may be added in an amount at least equimolar to, or preferably, an amount approximately equimolar to the fatty alcohol.

In another embodiment, altering the conditions such that the fatty alcohol forms micelles encompasses addition of a sulfonate. In a specific embodiment, sulfonate may be added in an amount at least approximately equimolar to the amount of the fatty alcohol.

A wide variety of fatty alcohols can be effectively used in connection with the methods of this invention as long as the structure contains an alcohol group attached to a hydrocarbon chain. Although there is no limit as to the length of the hydrocarbon chain present in the fatty alcohol, in some embodiments, the hydrocarbon chain has three or more, ten or more, twenty or more, or twenty-five or more carbons. In some embodiments, the hydrocarbon chain may be saturated or unsaturated. In other embodiments, the hydrocarbon chain may be straight or branched. In other embodiment, one or more hydrogen atoms in the hydrocarbon chain may be substituted with other chemical moieties. A specific example of a fatty alcohol that can be used in connection with the methods of this invention include, but are not limited to, octanol.

Initially, fatty acid, fatty acid salt or fatty alcohol used in methods of the invention can be added at an equimolar amount to the amount of the compound to be solubilized. Thereafter, fatty acid, fatty acid salt or fatty alcohol can be added empirically until the desired solubilization of the compound is achieved.

Various compounds can be solubilized using the methods of this invention. Such compounds include, but are not limited to, hydrophobic molecules, hydrophilic molecules, neutral molecules, small molecules or biologics. Specific examples of compounds that can be solubilized using methods of the invention include, but are not limited to, anticancer agents, anti-inflammatory agents, antifungal agents, anti-virals, anti-depressants, anti-psychotics, analgesics, antiemetics, antihypertensive agents, antibodies (including derivatives and fragments), immune-suppressants, Fc-fusion proteins, proteins, nucleic acids (single or double stranded DNA or RNA and derivatives thereof), cosmetic additives, food additives, amino acids, hormones and steroids. Specific examples of compounds that can be solubilized using the methods of this invention include, but are not limited to, acetaminophen, acetylsalicylic acid, amphotericin, aspirin, biphenyl dimethyl dicarboxylic acid, calcitonins, camptothecin, captopril, cephazoline, chloroquinine, chlorothiazole, cisplatin, co-agulation factors VIII and IX, cyclophosphamide, cyclosporins, d-alpha-tocopherol, daunomycin, dexamethasone, dichlofenac, digoxin, doxorubicin, estradiol, estrogen, etoposide, feldene, flubiprofen, 5-fluorouracil, fluoxetine, fusidic acid, gentamicin, glyburide, granisetron, growth hormones, ibuprofen, indomethacin, insulin, interferon, itraconazole, ketoconazole, ketoprofen, methotrexate, metronidazole, minoxidil, mitomycin, nafcillin, naproxen, ondansetron, oxyphenbutazone, paclitaxel, parazosin, physostigmine, piroxicam, prednisolone, primaquine, progestone, propranolol, prostaglandins, quinine, ramipril, taxotane, tenoxicam, terazosin, testosterone, triamcinolone, urokinase and vincristin. In specific embodiments, two or more compounds are solubilized together or are solubilized independently and then mixed for administration as a combination.

Moreover, it was discovered that methods of this invention can also be used with non-hydrophobic compounds, and thus enhance the solubility of the non-hydrophobic compounds. Accordingly, in specific embodiments, the solubility of a non-hydrophobic compound is enhanced using methods of the invention. The methods preferably result in at least 70%, 80%, 90%, 95% or 99% of the compound being in solution. In other embodiments, the methods preferably result in 20%, 30%, 50%, 100%, 150%, 200% or more increase in solubility of a compound as compared to the solubility of the same compound in a reference solvent, as determined by any methods known in the art. In yet other embodiments, the methods preferably result in 20%, 30%, 50%, 100%, 150%, 200% or more increase in solubility of a compound as compared to the solubility of the same compound in a reference solvent, without using the methods of the invention as determined by any methods known in the art. In one embodiment, the reference solvent is water. In another embodiment, the reference solvent is a solvent other than water, such as, but not limited to, an organic solvent.

4.2 Formulations of the Invention

The methods of this invention result in an increased solubility of various compounds. Accordingly, formulations, such as pharmaceutical compositions, comprising a compound solubilized at a concentration higher than the conventionally known concentration of the compound in water and other reference solvents are encompassed by the present invention. In some specific embodiments, this invention encompasses: a pharmaceutical composition comprising paclitaxel, wherein the concentration of paclitaxel solubilized is greater than 6 mg/mL; a pharmaceutical composition comprising cyclosporin A, wherein the concentration of cyclosporin A solubilized is greater than 50 mg/mL; a pharmaceutical composition comprising ketoprofen, wherein the concentration of ketoprofen solubilized is greater than 100 mg/mL; a pharmaceutical composition comprising acetylsalicylic acid, wherein the concentration of acetylsalicylic acid solubilized is greater than 25 mg/mL; and a pharmaceutical composition comprising digoxin, wherein the concentration of digoxin solubilized is greater than 1 mg/mL.

In addition to the increased solubility, the methods of this invention provide formulation of a compound, which possesses an increased stability as compared to the conventionally known formulations of the same compound. Accordingly, this invention also encompasses a stable pharmaceutical composition comprising paclitaxel, cyclosporin A, ketoprofen, acetylsalicylic acid, propofol, β-Lapachone or digoxin.

As used herein, the term "stable" or "stability" means that the active ingredient (e.g., the compound solubilized) of the composition, when prepared using the methods of this invention, remains solubilized in the medium for a period longer than when the composition is prepared using other methods known in the art. The stability of the composition of this invention can be determined using any well-known methods in the art One example of such methods is to examine the composition visually. Presumably, when the composition remains clear after a determined period of time, as opposed to becoming turbid, the active ingredient of the composition remains solubilized in the medium. Alternatively, the amount of the active ingredient remaining solubilized after a period of time can be determined using any analytical methods that can provide such information, for example, by HPLC. In some embodiments, greater than about 70 percent, about 80 percent, about 90 percent, about 95 percent or even about 99 percent of the active ingredient of the compositions of this invention remains solubilized in the solution for at least one week at room temperature after dilution with a diluent.

Furthermore, the methods of this invention provide many advantages over methods of solubilization conventionally known in the art. For example, the methods of this invention eliminate or reduce the need for toxic solvents such as CREMOPHOR® EL, N-methylpyrrolidone, dimethylformamide and DMSO in the formulation. Furthermore, co-solvents such as ethanol or PEG, co-detergents or surfactants such as Polysorbates or vitamin E, and oils such as Castor oil or corn oil, proteins such as HSA and other toxic substances are not necessary for the solubilization of a molecule according to the methods of this invention. Therefore, the methods of this invention provides an easy and convenient way to solubilize a compound, while providing a safer resultant formulation, by eliminating many harmful additives currently used for the solubilization of a compound. Therefore, this invention encompasses formulations (e.g., pharmaceutical compositions) comprising a compound (e.g., paclitaxel, cyclosporin A, ketoprofen, acetylsalicylic acid, propofol, β-Lapachone or digoxin), which contain no co-solvent, detergent, surfactant or oil.

Moreover, the solubilized product obtained using the methods of this invention is easily lyophilized, i.e., no additional bulking agents or surfactants and shorter lyophilization time (for example less than 12 hours, 16 hours, 24 hours, 30 hours, 36 hours or 48 hours, preferably, 24 to 36 hours), and readily reconstituted after lyophilization, ie., shorter reconstitution time (preferably, less than 30 seconds, less than 1 minute, less than 2 minutes, less than 10 minutes, less than 30 minutes, or less than 1 hour), in, for example, an aqueous medium such as water for injection, 0.9% saline or 5% dextrose. Accordingly, this invention also encompasses formulations prepared by a method of this invention, which can be easily lyophilized. In another embodiment, this invention encompasses formulations comprising a lyophilized composition of this invention, which can be conveniently reconstituted.

Compositions of the invention should be formulated according to the final use of the solubilized compounds. For example, the formulations of the invention may have pharmaceutical, cosmetic, industrial, consumer product-related, food-related, or dietary supplement-related applications. Any methods of making and formulating the compositions according to the specific use well-known in the art may be employed to formulate the compositions of the invention. By way of example, not limitation, pharmaceutical compositions are described below.

4.2.1 Pharmaceutical Compositions

Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols ( e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds solubilized and lyophilized according to methods of this invention from degradation within the gastrointestinal tract. In another example, the formulations of this invention may be administered in a liposomal formulation to shield the compounds from degradative enzymes, facilitate transport in circulatory system, and effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Suitable excipients, carriers or diluents may be added in the pharmaceutical compositions. Suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The compositions can additionally include lubricating agents, wetting agents, emulsifying and suspending agents, preserving agents, sweetening agents or flavoring agents. The compositions of the invention may be formulated so as to provide quick, sustained or delayed response of the active ingredient after administration to the patient.

4.2.1.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Disintegrates or lubricants can be used in pharmaceutical compositions and dosage forms of the invention.

4.2.1.2 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; and water-miscible vehicles such as, but not limited to, glycerol, ethyl alcohol, polyethylene glycol, and polypropylene glycol.

Compounds that further increase the solubility of one or more of the active ingredients disclosed herein can also be incorporated into the parenteral dosage forms of the invention.

4.2.1.3 Transdermal, Topical and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with formulations of the invention. For example, additional penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.2.1.4 Delayed Release Dosage Forms

Compositions of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compositions of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.2.15 Kits

In some cases, compositions of the invention are preferably not administered to a patient at the same time or by the same route of administration. This invention therefore encompasses kits which, when used by the medical practitioner, can simplify the administration of appropriate amounts of active ingredients to a patient A typical kit of the invention comprises a single unit dosage form of a composition of this invention, and a single unit dosage form of another agent that may be used in combination with the composition of the invention. Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form (e.g., lyophluized form) that must be reconstituted for parenteral administration, the kit can comprise a sealed container of a suitable vehicle in which the lyophilized compound can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, glycerol, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the formulations of the invention do not contain any ethanol or other co-solvents, oils or proteins.

The invention is further defined by reference to the following non-limiting examples. It will be apparent to those skilled in the art that many modifications, both to materials and methods, can be practiced without departing from the spirit and scope of this invention.

5. EXAMPLES

5.1 Cyclosporin A in Oleic Acid

Cyclosporin A (10 mg) was added to 35 μL of oleic acid and mixed using a VORTEX®. Ethanolamine (8 μL) was subsequently added and mixed using a VORTEX®. After mixing, the sample was dispersed in 466 μL of water for injection. Cyclosporin A was soluble and the formulation clear at 20 mg/mL. Cyclosporin A remained soluble, and the formulation was stable, upon dilution (1:10 in saline) up to 24 hours as analyzed by a reverse phase high performance liquid chromatography method.

5.2 Solubilization of Cyclosporin A in Caprylic Acid

Cyclosporin A (20 mg) was added to 144 μL of caprylic acid and mixed using a VORTEX®. Ethanolamine (62 μL) was subsequently added and mixed using a VORTEX®. After mixing, the sample was dispersed in 784 μL of water for injection. Cyclosporin was soluble and the formulation clear at 20 mg/mL. Cyclosporin A remained soluble, and the formulation was stable, upon dilution (1:1 in saline) up to 24 hours as analyzed by a reverse phase high performance liquid chromatography method.

5.3 Solubilization of Cyclosporin A in Sodium Oleate

Cyclosporin A (70 mg) was added to 1 mL of 0.5 M sodium oleate and mixed using a VORTEX®. Cyclosporin A was soluble and the formulation clear at 70 mg/mL. Cyclosporin A remained soluble, and the formulation was stable, upon dilution (1:10 in saline) up to 24 hours as analyzed by a reverse phase high performance liquid chromatography method.

5.4 Solubilization of Digoxin in Oleic Acid

Digoxin (1 mg) was added to 28 μL of oleic acid and mixed using VORTEX. Ethanolamine (6 μL) was subsequently added and mixed using a VORTEX®. After mixing, the sample was dispersed in 966 μL of water for injection. Digoxin was soluble and the formulation clear at 1 mg/mL. Digoxin remained soluble, and the formulation was stable, upon dilution (1:4 in saline) up to 24 hours as analyzed by a reverse phase high performance liquid chromatography method.

5.5 Solubilization of Digoxin in Sodium Oleate

Digoxin (1 mg) was added to 1 mL of 0.25 M sodium oleate and mixed using a VORTEX®. Digoxin was soluble and the formulation clear at 1 mg/mL. Digoxin remained soluble, and the formulation was stable, upon dilution (1:10 in saline) up to 24 hours as analyzed by a reverse phase high performance liquid chromatography method.

5.6 Solubilization of N-Acetylsalicylic Acid in Oleic Acid

N-acetylsalicylic acid (18 mg) was added to 31 μL of oleic acid and mixed using a VORTEX®. Ethanolamine (6 μL) was subsequently added and mixed using a VORTEX®. After mixing, the sample was dispersed in 963 μL of water for injection. N-acetylsalicylic acid was soluble and the formulation clear at 18 mg/mL. N-acetylsalicylic acid remained soluble, and the formulation was stable, upon dilution (1:10 in saline) up to 24 hours as analyzed by a reverse phase high performance liquid chromatography method.

5.7 Solubilization of N-Acetylsalicylic Acid in Sodium Oleate

N-acetylsalicylic acid (25 mg) was added to 1 mL of 0.25 M sodium oleate and mixed using a VORTEX®. N-acetylsalicylic acid was soluble and the formulation clear at 25 mg/mL. N-acetylsalicylic acid remained soluble, and the formulation was stable, upon dilution (1:10 in saline) up to 24 hours as analyzed by a reverse phase high performance liquid chromatography method.

5.8 Solubilization of Paclitaxel in Oleic Acid

Paclitaxel (18 mg) was added to 31 μL of oleic acid and mixed using a VORTEX®. Ethanolamine (6 μL) was subsequently added and mixed using a VORTEX®. After mixing, the sample was dispersed in 963 μL of water for injection. Paclitaxel was soluble and the formulation clear at 18 mg/mL. Paclitaxel remained soluble, and the formulation was stable, upon dilution (1:10 in saline) up to 24 hours as analyzed by a reverse phase high performance liquid chromatography method.

5.9 Solubilization of Paclitaxel in Sodium Oleate

Paclitaxel (5.6 mg) was added to 1 mL of 0.1 M sodium oleate and mixed using a VORTEX®. Paclitaxel was soluble and the formulation clear at 5.6 mg/mL. Paclitaxel remained soluble, and the formulation was stable, upon dilution (1:10 in saline) up to 24 hours as analyzed by a reverse phase high performance liquid chromatography method.

5.10 Solubilization of Paclitaxel in Sodium Caprylate

Paclitaxel (2 mg) was added to 1 mL of 1 M sodium caprylate and mixed by a VORTEX®. Paclitaxel was soluble and the formulation clear at 2 mg/mL. Paclitaxel remained soluble, and the formulation was stable, upon dilution (1:2 in saline) up to 24 hours as analyzed by a reverse phase high performance liquid chromatography method.

5.11 Solubilization of Paclitaxel in Sodium Linoleate

Paclitaxel (7.2 mg) was added to 1 mL of 1 M sodium linoleate and mixed using a VORTEX®. Paclitaxel was soluble and the formulation clear at 7.2 mg/mL. Paclitaxel remained soluble, and the formulation was stable, upon dilution (1:10 in saline) up to 24 hours as analyzed by a reverse phase high performance liquid chromatography method.

5.12 Dispersion in Basic Solution after Solubilization

Hydrophobic or lipophilic compounds can be solubilized either directly in sodium (or any ion) salt of fatty acid, or initially solubilized in fatty acid with or without co-solvent, and subsequently dispersed in equimolar (to fatty acid) amounts of sodium hydroxide (or any base) solution prepared in water or isotonic glycerol, or any pharmaceutically acceptable isotonic solution to achieve a desired concentration of the solubilized compound.

For example, β-Lapachone was dissolved (25 mg/mL) in ethanol:oleic acid (EtOH:OA) at volume to volume ratios of 70%:30%, 75%:25%, or 80%:20% EtOH:OA. A parenterally deliverable aqueous solution was achieved by dispersing the β-Lapachone-EtOH-OA mixture in equimolar (to oleic acid) amount of sodium hydroxide solution prepared in water, isotonic glycerol, or any pharmaceutically acceptable isotonic solution. The dispersed β-Lapachone was stable at least for 4 hours, 8 hours or 12 hours based on RP-HPLC.

In another example, β-Lapachone was dissolved (50 mg/mL) in dimethylsulfoxide:oleic acid (DMSO:OA) at volume to volume ratios of 60%:40, 70%:30% DMSO:OA or in DMSO:EtOH:OA (30%:30%:40% v/v). A parenterally deliverable aqueous solution was achieved by dispersing β-Lapachone-OA-DMSO/EtOH mixture in equimolar (to oleic acid) amount of sodium hydroxide solution prepared in water, isotonic glycerol or any pharmaceutically acceptable isotonic solution. The final concentration of the dispersed β-Lapachone was 1.5 mg/mL, 2.0 mg/mL or 2.5 mg/mL, and β-Lapachone was stable at least for 4 hours, 8 hours or 12 hours based on RP-HPLC.

5.13 Solubilization in Fatty Acid Dissolved in Isotonic Solutions

Hydrophobic or lipophilic compounds can be solubilized directly in sodium (or any ion) salt of fatty acid, dissolved in any physiologically acceptable isotonic solution (e.g., D5W), to achieve a desired concentration of the solubilized compound.

For example, Propofol (1% v/v or 10 mg/mL) was dissolved in 100 mM sodium oleate in 5% (w/v) dextrose in water for injection. The resulting solution containing 1% Propofol was lyophilized. The reconstituted lyophilized Propofol was stable without degradation or impurities based on RP-HPLC analysis.

5.14 Solubilization in Fatty Acid Dissolved in Organic Solvents

Hydrophobic or lipophilic compounds can be solubilized directly in sodium (or any ion) salt of fatty acid dissolved in an organic solvent. The organic solvent is subsequently removed using rotary evaporation, spray drying, or any other pharmaceutically acceptable processes. The drug-sodium salt of fatty acid mixture is subsequently dispersed in water, isotonic glycerol, or any pharmaceutically acceptable isotonic solution to achieve a desired concentration of the solubilized compound. A specific example is given below.

For example, Paclitaxel (5 mg/mL) was dissolved in 100 mM sodium oleate in 100% ethanol. Ethanol was completely evaporated using rotary evaporation at 20° C. The Paclitaxel-sodium oleate was reconstituted with WFI or 2.5% glycerol to provide 5 mg/mL, 10 mg/mL, or 20 mg/mL concentration of Paclitaxel. The reconstituted Paclitaxel remained in solution for 2 hours, 4 hours, 6 hours, 8 hours or 24 hours.

5.15 Efficacy of Paclitaxel Formulated in a Fatty Acid Salt

A study was performed to determine the efficacy of 22 mg/kg paclitaxel in 100 mM sodium oleate. In this study, the efficacy of this new formulation was compared to the conventional paclitaxel formulation in Cremophor® EL and ethanol (Taxol®).

Female nu/nu mice (Charles River laboratories, Wilmington Mass.) were 6-7 weeks old and weighed between 20 to 23 grams on day 0 of study. Human MX-1 breast carcinoma cells were used. Each of the forty mice was injected with 10 million cells on the right thigh. Mice were sorted into four groups of ten.

Group 1 mice received no treatment. Group 2 received lyophilized Paclitaxel in 100 mM sodium oleate, immediately after reconstitution with 2.5% glycerol to 2 mg/mL. Final concentration of sodium oleate is 40 mM. Group 3 received Taxol® immediately after dilution with physiological saline to 2 mg/mL. Group 4 received lyophilized 100 mM sodium oleate placebo vehicle immediately following reconstitution in 2.5 mL of 2.5% glycerol. Final concentration of sodium oleate in placebo was also 40 mM. The compounds were administered intravenously through the tail vein on days 9, 11, 13 and 15, after implantation with Human MX-1 breast carcinoma cells. A dosing mass of 22 mg/kg mouse was scaled to the body weight of each animal. Dosing volumes were in the range of 200 to 225 µL. The protocol is summarized in the table shown below:

PROTOCOL DESIGN

| | | Treatment Regimen | | | |
|---|---|---|---|---|---|
| Group | n | Agent | mg/kg | Route | Schedule(days) |
| 1 | 10 | None | — | i.v | 9, 11, 13, 15 |
| 2 | 10 | Paclitaxel in 100 mM sodium oleate | 22 | i.v | 9, 11, 13, 15 |
| 3 | 10 | Taxol ® | 22 | i.v | 9, 11, 13, 15 |
| 4 | 10 | 100 mM sodium oleate vehicle | — | i.v | 9, 11, 13, 15 |

The mice were evaluated based on the number of complete tumor regressions, tumor-free survivors, starting days of complete recurrence of 10/10 mice, days of complete regression of 10/10 mice, tumor free days of 10/10 mice and tumor recurrences. The results are summarized in the table shown below:

RESULTS

| Observations | Taxol ® (Paclitaxel in cremophore and ethanol) | Paclitaxel in sodium oleate |
|---|---|---|
| Complete tumor regression | 10/10 | 10/10 |
| Tumor free survivor* | 6/10 | 10/10 |
| Tumor recurrence | 4/10 | 0/10 |
| Starting Days of complete tumor regression of 10/10 mice | 20 | 20 |
| Mice number with complete tumor regression on 17th day | 7 | 9 |
| Tumor free days of 10/10 mice | 7 | >86 |

*Tumor free as of 106 days

As shown in the table, treatment with Paclitaxel in the sodium oleate formulation resulted in complete tumor regression and 100% survival (10/10) after 100 days. There were no tumor reoccurrences in this group (group 2). Treatment with conventional Taxol® (group 3) resulted in 106 day survival rates in only 60% of the animals. Both the non-treated controls (group 1) and the group (group 4) treated with control vehicle had no impact on tumor growth and the animals were sacrificed after 27 days.

These results show a possible increased efficacy for paclitaxel formulated in sodium oleate as compared to Taxol®. Furthermore, toxicological evaluations showed that the group receiving sodium oleate was comparable in its toxicity profiles of the animals which received Taxol®.

The embodiments of the invention described above are intended to be merely exemplary and those skilled in the art will recognize, or be able to ascertain using no more than routine experimentation, numerous equivalents to the specific procedures described herein. All such equivalents are considered to be within the scope of the invention and are encompassed by the following claims.

All of the patents, patent applications and publications referred to in this application are incorporated herein in their entireties. Moreover, citation or identification of any reference in this application is not an admission that such reference is available as prior art to this invention. The full scope of the invention is better understood with reference to the appended claims.

What is claimed is:

1. A method of formulating a composition having enhanced solubility of β-Lapachone, said method comprising: (A) contacting β-Lapachone with a fatty acid; (B) adding a solution of a base to the mixture resulting from step (A), wherein the amount of said base is equimolar to the amount of said fatty acid; and (C) steps (A) and (B) result in a composition with enhanced solubility of β-Lapachone.

2. The method of claim 1, wherein the fatty acid is used in combination with a co-solvent.

3. The method claim 2, wherein the co-solvent is ethanol or DMSO.

4. The method of claim 1, wherein the fatty acid comprises a hydrocarbon chain having more than three carbon atoms.

5. The method of claim 4, wherein the fatty acid is propionic acid, butyric acid, n-valeric acid, hexanoic acid, heptanoic acid, caprylic acid, nonanoic acid, decanoic acid, undecanoic acid, oleic acid, linoleic acid, linolenic acid or n-dodecanoic acid.

6. The method of claim 5, wherein the fatty acid is oleic acid.

7. The method of claim 1, wherein the base is sodium hydroxide.

8. The method of claim 7, wherein the sodium hydroxide is prepared in a pharmaceutically acceptable isotonic solution.

9. The method of claim 8, wherein the pharmaceutically acceptable isotonic solution is water or isotonic glycerol.

10. A composition comprising β-Lapachone, wherein said β-Lapachone is solubilized using a fatty acid and a base according to the method of claim 1.

11. The composition of claim 10, wherein the fatty acid is used in combination with a co-solvent.

12. The composition of claim 11, wherein the co-solvent is ethanol or DMSO.

13. The composition of claim 12, wherein the final concentration of β-Lapachone is from 1.5 mg/mL to 2.5 mg/mL.

14. The composition of claim 13, wherein higher than 70 percent of the solubilized β-Lapachone remains solubilized for at least 4 hours after the solubilization.

15. The composition of claim 14, wherein higher than 70 percent of the solubilized β-Lapachone remains solubilized for at least 8 hours after the solubilization.

16. The composition of claim 15, wherein higher than 70 percent of the solubilized β-Lapachone remains solubilized for at least 12 hours after the solubilization.

* * * * *